United States Patent [19]

Hsu

[11] Patent Number: 5,236,888
[45] Date of Patent: Aug. 17, 1993

[54] BIOCIDAL COMBINATIONS CONTAINING 4,5-DICHLORO-2-CYCLOHEXYL-3-ISO-THIAZOLONE AND CERTAIN COMMERCIAL BIOCIDES

[75] Inventor: Jemin C. Hsu, Fort Washington, Pa.

[73] Assignee: Rohm and Haas Company, Philadelphia, Pa.

[21] Appl. No.: 964,233

[22] Filed: Oct. 21, 1992

Related U.S. Application Data

[62] Division of Ser. No. 844,254, Mar. 2, 1992, Pat. No. 5,185,355, which is a division of Ser. No. 625,281, Dec. 10, 1990, Pat. No. 5,157,045.

[51] Int. Cl.$^5$ ............... A01N 43/00; A01N 43/32; A01N 43/66; A01N 43/80
[52] U.S. Cl. ............... 504/154; 504/155; 504/156; 504/161; 514/241; 514/372; 514/452; 514/727
[58] Field of Search ............... 514/372, 452, 727, 241; 71/67; 504/154, 155, 156, 161

[56] References Cited

U.S. PATENT DOCUMENTS

| | | | |
|---|---|---|---|
| 3,755,590 | 8/1973 | Brooks et al. | 514/241 |
| 3,772,443 | 11/1973 | Wessendorf et al. | 514/452 |
| 4,173,643 | 11/1979 | Law | 514/372 |
| 4,990,525 | 2/1991 | Hsu | 514/452 |

Primary Examiner—Allen J. Robinson
Attorney, Agent, or Firm—Michael B. Fein

[57] ABSTRACT

Synergistic microbicidal compositions are disclosed, comprising 4,5-dichloro-2-cyclohexyl-3-isothiazolone and one or more known microbicides for more effective, and broader control of microorganisms in various systems.

8 Claims, No Drawings

BIOCIDAL COMBINATIONS CONTAINING 4,5-DICHLORO-2-CYCLOHEXYL-3-ISOTHIAZOLONE AND CERTAIN COMMERCIAL BIOCIDES

This is a divisional of application Ser. No. 07/844,254, filed Mar. 2, 1992, now U.S. Pat. No. 5,185,355, which is a divisional of application Ser. No. 07/625,281, filed Dec. 10, 1990, now U.S. Pat. No. 5,157,045.

BACKGROUND OF THE INVENTION

1. Field of the Invention

This invention concerns microbicidal compositions which include an isothiazolone and one or more other biocides, and which are intended to provide more effective and broader control of microorganisms in various industrial systems and for household products, agricultural products, and biomedical products, etc. In particular, the present invention relates to the use of a composition of 4,5-dichloro-2-cyclohexyl-3-isothiazolone, with one or more of the following [14] compounds: 3-iodo-2-propynylbutylcarbamate, 1,2-dibromo-2,4-dicyanobutane, methylene-bis-thiocyanate, a mixture of 4,4-dimethyloxazoline and 4,4-dimethyl-N-methyloxazoline, 5-polyhydroxymethyleneoxy-methyl-1-aza-3,7-dioxabicyclo(3.3.0) octane, tetrachoroisophthalonitrile, 2-n-octyl-3-isothiazolone, 5-bromo-5-nitro-1,3-dioxane, 2-bromo-2-nitropropanediol, hexahydro-1,3,5-triethyl-s-triazine, 2,2-dibromo-3-nitrilopropionamide, benzylbromoacetate, p-chloro-m-xylenol, and 1,3,5-tris-(2-ethoxyl)-s-triazine.

The term "microbicidal" (or "antimicrobial" or "biocidal") as used herein is intended to encompass, but is not restricted to, all bactericidal, fungicidal and algicidal activity.

2. Prior Art

Isothiazolones are described in U.S. Pat. Nos. 3,761,488; 4,105,431; 4,252,694; 4,265,899 and 4,279,762, and elsewhere. Their use as microbicides is well known. The "second" components are commerical biocides.

It is the principal object of this invention to provide synergistic compositions which overcome disadvantages of known microbicidal compositions.

SUMMARY OF THE INVENTION

We have found that compositions formed from 4,5-dichloro-2-cyclohexyl-3-isothiazolone and one or more of the following compounds: 3-iodo-2-propynylbutylcarbamate, 1,2-dibromo-2,4-dicyanobutane, methylene-bis-thiocyanate, a mixture of 4,4-dimethyloxazoline and 4,4-dimethyl-N-methyloxazoline, 5-polyhydroxymethyleneoxy-methyl-1-aza-3,7-dioxabicyclo(3.3.0)octane, tetrachloroisophthalonitrile, 2-n-octyl-3-isothiazolone, 5-bromo-5-nitro-1,3-dioxane, 2-bromo-2-nitropropanediol, hexahydro-1,3,5-triethyl-s-triazine, 2,2-dibromo-3-nitrilopropionamide, benzylbromoacetate, p-chloro-m-xylenol, and 1,3,5-tris-(2-ethoxyl)-s-triazine unexpectedly afford synergistic antimicrobial activity against a wide range of microorganisms: the disruptive action on the organisms by the two or more compounds together is unexpectedly greater than the sum of both compounds taken alone. This synergy does not arise from the expected activity of the components nor from the expected improvement in activity. As a result of the synergy, the effective dose required can be lowered, which is not only more economical but also increases safety margins. The synergistic compositions of the present invention provide more effective and broader control of microorganisms in a number of systems.

The present invention thus provides a composition having microbicidal activity which includes 4,5-dichloro-2-cyclohexyl-3-isothiazolone and a second component selected from one or more of the group consisting of: 3-iodo-2-propynylbutylcarbamate, 1,2-dibromo-2,4-dicyanobutane, methylene-bis-thiocyanate, a mixture of 4,4-dimethyloxazoline and 4,4-dimethyl-N-methyloxazoline, 5-polyhydroxymethyleneoxy-methyl-1-aza-3,7-dioxabicyclo(3.3.0)octane, tetrachloroisophthalonitrile, 2-n-octyl-3-isothiazolone, 5-bromo-5-nitro-1,3-dioxane, 2-bromo-2-nitropropanediol, hexahydro-1,3,5-triethyl-s-triazine, 2,2-dibromo-3-nitrilopropionamide, benzylbromoacetate; p-chloro-m-xylenol; and 1,3,5-tris-(2-ethoxyl)-s-triazine wherein the weight ratio of 4,5-dichloro-2-cyclohexyl-3-isothiazolone to the second component is from about 8:1 to about 1:4000.

Important applications of the synergistic antimicrobial compositions of the present invention include but are not limited to: inhibiting the growth of bacteria and fungi in aqueous paints and coatings, adhesives, sealants, latex emulsions, and joint cements; preserving wood; preserving cutting fluids, controlling slime-producing bacteria and fungi in pulp and papermills and cooling towers; as a spray or dip treatment for textiles and leather to prevent mold growth; protecting paint films, especially exterior paints, from attach by fungi which occurs during weathering of the paint film; protecting processing equipment from slime deposits during manufacture of cane and beet sugar; preventing microorganism buildup and deposits in air washer or scrubber systems and in industrial fresh water supply systems; preserving fuel; controlling microorganisms contamination and deposits in oil field drilling fluids and muds, and in secondary petroleum recovery processes; preventing bacterial and fungal growth in paper coatings and coating processes; controlling bacterial and fungal growth and deposits during the manufacture of various specialty boards, e.g., cardboard and particle board; preventing sap stain discoloration on freshly cut wood of various kinds; controlling bacterial and fungal growth in clay and pigment slurries of various types; as a hard surface disinfectant to prevent growth of bacteria and fungi on walls, floors, etc.; as a preservative for cosmetic and toiletry raw materials, floor polishes, fabric softeners, household and industrial cleaners; in swimming pools to prevent algae growth; inhibiting the growth of harmful bacteria, yeasts, fungi on plants, trees, fruits, seeds, or soil; preserving agricultural formulations, electrodeposition systems, diagnostic and reagent products, medical devices; protecting animal dip compositions against the buildup of microorganisms, and in photoprocessing to prevent buildup of microorganisms, and the like.

The compositions of the invention may be added separately to any system or may be formulated as a simple mixture comprising its essential ingredients, and if desired a suitable carrier or solvent, or as an aqueous emulsion or dispersion.

The invention also provides a method of inhibiting the growth of bacteria, fungi or algae in a locus subject to contamination by bacteria, fungi or algae, which comprises incorporating into or onto the locus in an amount which is effective to adversely affect the growth of bacteria, fungi or algae any of the compositions defined above.

GENERAL DESCRIPTION OF THE PREFERRED EMBODIMENT

The composition of the invention can be formulated as a solution in a wide range of organic solvents. The solutions generally contain about 1 to 30% by weight of the active composition. It is generally more convenient to provide the compositions in a water-diluted form: this may be accomplished by adding an emulsifier to the organic solution followed by dilution with water.

In general, the weight ratio of 4,5-dichloro-2-cyclohexyl-3-isothiazolone to second component in the composition may be in the range of from about 8:1 to about 1:4000. The other specific and preferred ratios are given in the examples.

The synergism of two-component compositions is demonstrated by testing a wide range of concentrations and ratios of compounds, generated by two-fold serial dilutions in a Trypticase Soy Broth (Difco) growth medium of a microbicide in one dimension and another microbicide in the second dimension, against a bacterium *Escherichia coli* (ATCC 11229), or fungi *Candida albicans* (ATCC 11651), *Aspergillus niger* (ATCC 6275), or *Aureobasidium pullulans* (ATCC 9348). Each test tube was inoculated to make about $1-5 \times 10^7$ bacteria per ml or $1-5 \times 10^5$ fungi per ml. The lowest concentrations of each compound or mixtures to inhibit visible growth (turbidity) at 37° for *E. coli* and at 30° C. for the fungi for 7 days were taken as the minimum inhibitory concentration (MIC). The MIC were taken as end points of activity. End points for the mixtures of compound A (4,5-dichloro-2-cyclohexyl-3-isothiazolone) and compound B (second component microbicide) were then compared with the end points for the isothiazolone A alone and compound B alone. Synergism was determined by a commonly used and accepted method described by Kull, F. C.; Eisman, P. C.; Sylwestrowicz, H. D. and Mayer, R. L., in applied Microbiology 9:538-541 (1961) using the ratio determined by $Qa/QA + Qb/QB$ = Synergy Index (SI)

wherein
- QA = concentration of compound A in parts per million (ppm), acting alone, which produced an end point.
- Qa = concentration of compound A in ppm, in the mixture, which produced an end point.
- QB = concentration of compound B in ppm, acting alone, which produced an end point.
- Qb = concentration of compound B in ppm, in the mixture, which produced an end point when the sum of Qa/QA and Qb/QB is greater than one, antagonism is indicated. When the sum is equal to one additivity is indicated, and when less than one synergism is demonstrated.

The test results for demonstration of synergism of microbicide combinations are shown in Tables 1 to 14. Each table concerns the combination of 4,5-dichloro-2-cyclohexyl-3-isothiazolone and one other microbicide, and shows:

1. the identity of the second microbicide (compound B)
2. test against *E. coli*, *C. albicans* (C.alb), *A. niger* or *A. pullulans* (A. pullul)
3. the end-point activity in ppm measured by MIC for either compound alone or their combinations
4. the synergy index (SI) based on the formula SI = Qa/QA + Qb/QB
5. the range of weight ratios for synergism; it will be appreciated by those skilled in the art that the ratios given are approximate only.

TABLE 1

Compound A = 4,5-dichloro-2-cyclohexyl-3-isothiazolone
Compound B = 4,4-dimethyoxazoline + 4,4-dimethyl-N-methyloxazoline mixture

| ORGANISM | Compound A | Compound B | Synergy Index | Ratio (A:B) |
|---|---|---|---|---|
| C. albicans | 1 | 0 | | |
| | 0.5 | 500 | 0.75 | 1:1000 |
| | 0.25 | 1000 | 0.75 | 1:4000 |
| | 0 | 2000 | | |
| E. coli | 16 | 0 | | |
| | 8 | 250 | 0.75 | 1:31 |
| | 4 | 500 | 0.75 | 1:125 |
| | 0 | 1000 | | |

TABLE 2

Compound A = 4,5-dichloro-2-cyclohexyl-3-isothiazolone
Compound B = 5-bromo-5-nitro-1,5-dioxane

| ORGANISM | Compound A | Compound B | Synergy Index | Ratio (A:B) |
|---|---|---|---|---|
| C. albicans | 4 | 0 | | |
| | 2 | 6.2 | 0.56 | 1:3 |
| | 2 | 12.5 | 0.62 | 1:6 |
| | 1 | 12.5 | 0.37 | 1:12 |
| | 1 | 25 | 0.50 | 1:25 |
| | 0.5 | 25 | 0.37 | 1:50 |
| | 0.5 | 50 | 0.62 | 1:100 |
| | 0.25 | 50 | 0.56 | 1:200 |
| | 0 | 100 | | |
| E. coli | 16 | 0 | | |
| | 8 | 25 | 0.75 | 1:3 |
| | 4 | 50 | 0.75 | 1:12 |
| | 2 | 50 | 0.62 | 1:25 |
| | 1 | 50 | 0.56 | 1:50 |
| | 0 | 100 | | |

TABLE 3

Compound A = 4,5-dichloro-2-cyclohexyl-3-isothiazolone
Compound B = 2,2-dibromo-3-nitrilopropionamide

| ORGANISM | Compound A | Compound B | Synergy Index | Ratio (A:B) |
|---|---|---|---|---|
| C. albicans | 4 | 0 | | |
| | 2 | 31 | 0.52 | 1:16 |
| | 1 | 31 | 0.27 | 1:31 |
| | 1 | 62 | 0.31 | 1:62 |
| | 1 | 125 | 0.37 | 1:125 |
| | 0.5 | 125 | 0.25 | 1:250 |
| | 0.5 | 250 | 0.37 | 1:500 |
| | 0.25 | 250 | 0.31 | 1:1000 |
| | 0.25 | 500 | 0.56 | 1:2000 |
| | 0.12 | 500 | 0.53 | 1:4000 |
| | 0 | 1000 | | |
| E. coli | 16 | 0 | | |
| | 4 | 31 | 0.75 | 1:8 |
| | 0 | 62 | | |

TABLE 4

Compound A = 4,5-dichloro-2-cyclohexyl-3-isothiazolone
Compound B = 1,3,5-tris-(2-ethoxyl)-s-triazine

| ORGANISM | Compound A | Compound B | Synergy Index | Ratio (A:B) |
|---|---|---|---|---|
| C. albicans | 0.5 | 0 | | |
| | 0.25 | 500 | 0.75 | 1:2000 |

TABLE 4-continued

Compound A = 4,5-dichloro-2-cyclohexyl-3-isothiazolone
Compound B = 1,3,5-tris-(2-ethoxyl)-s-triazine

| ORGANISM | Compound A | Compound B | Synergy Index | Ratio (A:B) |
|---|---|---|---|---|
| | 0 | 2000 | | |
| E. coli | 16 | 0 | | |
| | 8 | 250 | 0.75 | 1:31 |
| | 4 | 500 | 0.75 | 1:125 |
| | 0 | 1000 | | |

TABLE 5

Compound A = 4,5-dichloro-2-cyclohexyl-3-isothiazolone
Compound B = methylene-bis-thiocyanate

| ORGANISM | Compound A | Compound B | Synergy Index | Ratio (A:B) |
|---|---|---|---|---|
| A. pullulans | 8 | 0 | | |
| | 4 | 16 | 0.75 | 1:4 |
| | 2 | 32 | 0.75 | 1:16 |
| | 1 | 32 | 0.62 | 1:32 |
| | 0.5 | 32 | 0.56 | 1:64 |
| | 0.25 | 32 | 0.53 | 1:125 |
| | 0 | 64 | | |
| C. albicans | 1 | 0 | | |
| | 0.5 | 4 | 0.63 | 1:8 |
| | 0.5 | 8 | 0.75 | 1:16 |
| | 0 | 32 | | |
| E. coli | 62 | 0 | | |
| | 32 | 32 | 0.75 | 1:1 |
| | 16 | 32 | 0.50 | 1:2 |
| | 16 | 62 | 0.75 | 1:4 |
| | 8 | 62 | 0.62 | 1:8 |
| | 4 | 62 | 0.56 | 1:16 |
| | 2 | 62 | 0.53 | 1:31 |
| | 0 | 125 | | |

TABLE 6

Compound A = 4,5-dichloro-2-cyclohexyl-3-isothiazolone
Compound B = benzylbromoacetate

| ORGANISM | Compound A | Compound B | Synergy Index | Ratio (A:B) |
|---|---|---|---|---|
| C. albicans | 1 | 0 | | |
| | 0.5 | 0.5 | 0.51 | 1:1 |
| | 0.5 | 1 | 0.53 | 1:2 |
| | 0.5 | 2 | 0.56 | 1:4 |
| | 0.5 | 4 | 0.62 | 1:8 |
| | 0.5 | 8 | 0.75 | 1:16 |
| | 0.25 | 16 | 0.75 | 1:64 |
| | 0 | 32 | | |
| E. coli | 16 | 0 | | |
| | 8 | 31 | 0.62 | 1:4 |
| | 8 | 62 | 0.75 | 1:8 |
| | 4 | 125 | 0.75 | 1:32 |
| | 0 | 250 | | |

TABLE 7

Compound A = 4,5-dichloro-2-cyclohexyl-3-isothiazolone
Compound B = tetrachloroisophthalonitrile

| ORGANISM | Compound A | Compound B | Synergy Index | Ratio (A:B) |
|---|---|---|---|---|
| A. pullulans | 8 | 0 | | |
| | 4 | 1 | 0.56 | 4:1 |
| | 4 | 2 | 0.63 | 2:1 |
| | 4 | 4 | 0.75 | 1:1 |
| | 2 | 4 | 0.50 | 1:2 |
| | 1 | 4 | 0.37 | 1:4 |
| | 1 | 8 | 0.62 | 1:8 |
| | 0.5 | 8 | 0.56 | 1:16 |
| | 0 | 16 | | |

TABLE 7-continued

Compound A = 4,5-dichloro-2-cyclohexyl-3-isothiazolone
Compound B = tetrachloroisophthalonitrile

| ORGANISM | Compound A | Compound B | Synergy Index | Ratio (A:B) |
|---|---|---|---|---|
| E. niger | 8 | 0 | | |
| | 4 | 2 | 0.63 | 2:1 |
| | 4 | 4 | 0.75 | 1:1 |
| | 2 | 4 | 0.50 | 1:2 |
| | 2 | 8 | 0.75 | 1:4 |
| | 0 | 16 | | |

TABLE 8

Compound A = 4,5-dichloro-2-cyclohexyl-3-isothiazolone
Compound B = 5-polyhydroxymethyleneoxy-methyl-l-aza-3,7-dioxabicyclo(3.3.0)octane

| ORGANISM | Compound A | Compound B | Synergy Index | Ratio (A:B) |
|---|---|---|---|---|
| C. albicans | 4 | 0 | | |
| | 2 | 500 | 0.75 | 1:250 |
| | 1 | 1000 | 0.75 | 1:1000 |
| | 0 | 2000 | | |
| E. coli | 16 | 0 | | |
| | 8 | 125 | 0.75 | 1:16 |
| | 4 | 250 | 0.75 | 1:62 |
| | 0 | 500 | | |

TABLE 9

Compound A = 4,5-dichloro-2-cyclohexyl-3-isothiazolone
Compound B = p-chloro-m-xylenol

| ORGANISM | Compound A | Compound B | Synergy Index | Ratio (A:B) |
|---|---|---|---|---|
| C. albicans | 2 | 0 | | |
| | 1 | 8 | 0.62 | 1:8 |
| | 1 | 16 | 0.75 | 1:16 |
| | 0.5 | 31 | 0.75 | 1:62 |
| | 0.25 | 31 | 0.62 | 1:125 |
| | 0 | 62 | | |
| E. coli | 16 | 0 | | |
| | 8 | 125 | 1.00 | 1:16 |
| | 0 | 250 | | |

TABLE 10

Compound A = 4,5-dichloro-2-cyclohexyl-3-isothiazolone
Compound B = 2-n-octyl-3-isothiazolone

| ORGANISM | Compound A | Compound B | Synergy Index | Ratio (A:B) |
|---|---|---|---|---|
| C. albicans | 0.5 | 0 | | |
| | 0.25 | 0.12 | 0.75 | 2:1 |
| | 0 | 0.5 | | |
| A. pullulans | 8 | 0 | | |
| | 4 | 1 | 0.75 | 4:1 |
| | 2 | 1 | 0.50 | 2:1 |
| | 2 | 2 | 0.75 | 1:1 |
| | 0 | 4 | | |
| E. coli | 16 | 0 | | |
| | 4 | 125 | 0.75 | 1:31 |
| | 0 | 250 | | |

TABLE 11

Compound A = 4,5-dichloro-2-cyclohexyl-3-isothiazolone
Compound B = 3-iodo-2-propynylbutylcarbamate

| ORGANISM | Compound A | Compound B | Synergy Index | Ratio (A:B) |
|---|---|---|---|---|
| C. albicans | 1 | 0 | | |

TABLE 11-continued

Compound A = 4,5-dichloro-2-cyclohexyl-3-isothiazolone
Compound B = 3-iodo-2-propynylbutylcarbamate

| ORGANISM | end-point activity in ppm | | Synergy Index | Ratio (A:B) |
|---|---|---|---|---|
| | Compound A | Compound B | | |
| | 0.5 | 0.5 | 0.56 | 1:1 |
| | 0.5 | 1 | 0.62 | 1:2 |
| | 0.5 | 2 | 0.75 | 1:4 |
| | 0.25 | 4 | 0.75 | 1:16 |
| | 0.12 | 4 | 0.62 | 1:32 |
| | 0 | 8 | | |
| A. pullulans | 8 | 0 | | |
| | 4 | 0.5 | 0.62 | 8:1 |
| | 4 | 1 | 0.75 | 4:1 |
| | 2 | 1 | 0.50 | 2:1 |
| | 2 | 2 | 0.75 | 1:1 |
| | 0 | 4 | | |
| A. niger | 8 | 0 | | |
| | 4 | 2 | 0.75 | 2:1 |
| | 2 | 4 | 0.75 | 1:2 |
| | 1 | 4 | 0.62 | 1:4 |
| | 0 | 8 | | |
| E. coli | 16 | 0 | | |
| | 4 | 125 | 0.75 | 1:31 |
| | 2 | 125 | 0.62 | 1:62 |
| | 0 | 250 | | |

TABLE 12

Compound A = 4,5-dichloro-2-cyclohexyl-3-isothiazolone
Compound B = 1,2-dibromo-2,4-dicyanobutane

| ORGANISM | end-point activity in ppm | | Synergy Index | Ratio (A:B) |
|---|---|---|---|---|
| | Compound A | Compound B | | |
| C. albicans | 1 | 0 | | |
| | 0.5 | 4 | 0.62 | 1:8 |
| | 0.5 | 8 | 0.75 | 1:16 |
| | 0.25 | 16 | 0.75 | 1:62 |
| | 0 | 32 | | |
| A. pullulans | 8 | 0 | | |
| | 4 | 16 | 0.75 | 1:4 |
| | 2 | 32 | 0.75 | 1:16 |
| | 0 | 64 | | |
| E. coli | 16 | 0 | | |
| | 8 | 16 | 0.75 | 1:2 |
| | 0 | 62 | | |

TABLE 13

Compound A = 4,5-dichloro-2-cyclohexyl-3-isothiazolone
Compound B = hexahydro-1,3,5-triethyl-s-triazine

| ORGANISM | end-point activity in ppm | | Synergy Index | Ratio (A:B) |
|---|---|---|---|---|
| | Compound A | Compound B | | |
| C. albicans | 0.5 | 0 | | |
| | 0.25 | 250 | 0.62 | 1:1000 |
| | 0.25 | 500 | 0.75 | 1:2000 |
| | 0 | 2000 | | |
| E. coli | 16 | 0 | | |
| | 8 | 125 | 0.75 | 1:16 |
| | 4 | 250 | 0.75 | 1:62 |
| | 0 | 500 | | |

TABLE 14

Compound A = 4,5-dichloro-2-cyclohexyl-3-isothiazolone
Compound B = 2-bromo-2-nitropropanediol

| ORGANISM | end-point activity in ppm | | Synergy Index | Ratio (A:B) |
|---|---|---|---|---|
| | Compound A | Compound B | | |
| C. albicans | 4 | 0 | | |
| | 2 | 12.5 | 0.56 | 1:6 |

TABLE 14-continued

Compound A = 4,5-dichloro-2-cyclohexyl-3-isothiazolone
Compound B = 2-bromo-2-nitropropanediol

| ORGANISM | end-point activity in ppm | | Synergy Index | Ratio (A:B) |
|---|---|---|---|---|
| | Compound A | Compound B | | |
| | 2 | 25 | 0.62 | 1:12 |
| | 1 | 25 | 0.37 | 1:25 |
| | 0.5 | 25 | 0.25 | 1:50 |
| | 0.5 | 50 | 0.37 | 1:100 |
| | 0.25 | 50 | 0.31 | 1:200 |
| | 0.25 | 100 | 0.56 | 1:400 |
| | 0 | 200 | | |
| E. coli | 62 | 0 | | |
| | 16 | 50 | 0.75 | 1:3 |
| | 8 | 50 | 0.62 | 1:6 |
| | 4 | 50 | 0.56 | 1:12 |
| | 2 | 50 | 0.53 | 1:25 |
| | 1 | 50 | 0.52 | 1:50 |
| | 0 | 100 | | |

As can be seen by review of Table 1-14, the compositions of the invention demonstrate synergistic microbicidal activity as measured by minimum inhibitory concentrations (MIC) and show surprisingly greater activity than the algebraic sum of the individual components which make up each composition.

The synergistic activities of the compositions of the invention in most cases are applicable to bacteria, fungi, and a mixture of bacteria and fungi. Thus, the combinations not only lower the use-level of biocide but also broaden the spectrum of activity. This is especially useful in situations where either component alone does not achieve the best results due to weak activity against certain organisms.

What is claimed is:

1. A microbicidal composition comprising a synergistic mixture, the first component of which is 4,5-dichloro-2-cyclohexyl-3-isothiazolone and the second component of which is selected from the group consisting of 5-bromo-5-nitro-1,3-dioxane, 2-bromo-2-nitropropanediol, and hexahydro-1,3,5-triethyl-s-triazine, wherein the synergistic weight ratio of first component to second component is in the range of from about 8:1 to about 1:4000.

2. The composition of claim 1, wherein the ratio of the first component to the second component, 5-bromo-4-nitro-1,3-dioxane, is in the range of from about 1:3 to about 1:200.

3. The composition of claim 1, wherein the ratio of the first component to the second component, hexahydro-1,3,5-triethyl-s-triazine, is in the range of from about 1:16 to about 1:2000.

4. The composition of claim 1, wherein the ratio of the first component to the second component, 2-bromo-2-nitropropanediol, is in the range of from about 1:3 to about 1:400.

5. A composition useful for inhibiting the growth of microorganisms selected from the group consisting of bacteria, fungi and mixture thereof in a locus comprising about 1 to about 30% of the composition of claim 1 and a carrier.

6. The composition according to claim 5, wherein the carrier further comprises an emulsifier and water.

7. A method for inhibiting the growth of a member selected from the group consisting of bacteria, fungi, algae and mixtures thereof in a locus subject to contamination by said member, which comprises incorporating onto or into the locus, in an amount which is effective to adversely affect the growth of said member, the composition of claim 1.

8. The method of claim 7 wherein the locus is an aqueous medium, and the composition additionally contains an emulsifier and water.

* * * * *